United States Patent
Rasmussen et al.

(10) Patent No.: US 10,188,502 B2
(45) Date of Patent: Jan. 29, 2019

(54) AORTIC GRAFT DEVICE

(71) Applicant: Cook Medical Technologies LLC, Bloomington, IN (US)

(72) Inventors: Erik E. Rasmussen, Slagelse (DK); Frank K. Christiansen, Haslev (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/696,647

(22) Filed: Sep. 6, 2017

(65) Prior Publication Data

US 2017/0367811 A1  Dec. 28, 2017

Related U.S. Application Data

(63) Continuation of application No. 14/695,735, filed on Apr. 24, 2015, now Pat. No. 9,848,977, which is a continuation of application No. 11/998,532, filed on Nov. 30, 2007, now Pat. No. 9,044,311.

(60) Provisional application No. 60/861,853, filed on Nov. 30, 2006.

(51) Int. Cl.
| | |
|---|---|
| *A61F 2/82* | (2013.01) |
| *A61F 2/07* | (2013.01) |
| *A61F 2/06* | (2013.01) |
| *A61F 2/89* | (2013.01) |

(52) U.S. Cl.
CPC ............... *A61F 2/07* (2013.01); *A61F 2/06* (2013.01); *A61F 2/89* (2013.01); *A61F 2002/061* (2013.01); *A61F 2002/075* (2013.01); *A61F 2210/0014* (2013.01); *A61F 2220/0008* (2013.01)

(58) Field of Classification Search
CPC ....................................................... A61F 2/82
See application file for complete search history.

(56) References Cited

U.S. PATENT DOCUMENTS

| | | |
|---|---|---|
| 5,433,909 A | 7/1995 | Martakos et al. |
| 5,747,128 A | 5/1998 | Campbell et al. |
| 5,824,040 A | 10/1998 | Cox et al. |
| 5,984,955 A | 11/1999 | Wisselink |
| 6,016,810 A | 1/2000 | Ravenscroft |
| 6,099,548 A | 8/2000 | Taheri |
| 6,517,571 B1 | 2/2003 | Brauker et al. |
| 6,773,457 B2 | 8/2004 | Ivancev et al. |
| 2007/0010873 A1 | 1/2007 | Neri |

FOREIGN PATENT DOCUMENTS

FR 2777450 10/2000

*Primary Examiner* — Matthew Schall
(74) *Attorney, Agent, or Firm* — Brinks Gilson & Lione

(57) ABSTRACT

An aortic arch device that is a unitary tube of graft material having a crimped unstented portion and a stented portion, a collar at the junction of the crimped unstented portion and the stented portion, at least one fenestration or lateral opening in the graft material to accommodate arteries in the aortic arch. Branches may extend from the fenestrations.

20 Claims, 3 Drawing Sheets

AORTIC GRAFT DEVICE

RELATED APPLICATIONS

The present patent document is a continuation of U.S. application Ser. No. 14/695,735, filed Apr. 24, 2015, which is a continuation of U.S. application Ser. No. 11/998,532, filed Nov. 30, 2007, now U.S. Pat. No. 9,044,311, which claims the benefit of the filing date under 35 U.S.C. § 119(e) of Provisional U.S. Patent Application Ser. No. 60/861,853, filed Nov. 30, 2006. All of the foregoing applications are hereby incorporated by reference.

TECHNICAL FIELD

The present invention relates to an aortic graft device provided with a graft portion and a corrugated portion extending from the graft portion.

BACKGROUND OF THE INVENTION

An aortic graft is an endovascular prosthesis for placement in the aorta, in a weakened area, such as an aneurysm or an aortic dissection. An aortic aneurysm is an abnormal dilation or enlargement of the arterial wall of the aorta. If a significantly large aneurysm is not treated, it can rupture with abrupt fatal blood loss, either into the abdominal or thoracic cavity of the patient.

An aortic graft is typically made of a tube of pliable material provided with a stent for anchoring the graft in its intended position within the blood vessel by exerting an outwardly directed radial pressure against the surrounding aortic wall. This requires in the region of the stent a relatively healthy aortic wall that can withstand the radial pressure for years. Patients diagnosed with aortic aneurysms are often in poor health due to other illnesses which increase the risk of complications associated with an operation. Most prior art stent grafts are designed for abdominal aortic aneurysms (AAA) involving the pararenal and the infrarenal aorta. Examples of such grafts are described in U.S. Pat. Nos. 5,984,955 and 6,016,810. Many of these grafts are bifurcated and extend to the iliac arteries. Aortic grafts of these types can typically be placed using transluminal, minimally invasive, procedures where the grafts are percutaneously introduced via a femoral puncture site, and the entire procedure can be performed using local anaesthesia.

With respect to aortic grafts for the repair of thoracoabdominal aortic aneurysms (aneurysms in the descending thoracic aorta) and other thoracic aortic aneurysms (aneurysms in the ascending thoracic aorta including the aortic arch) only a few proposals for minimally invasive procedures have been made.

U.S. Pat. No. 6,099,548 proposes to advance the graft into the ascending thoracic aorta and to lock it to the aortic wall by expanding a stent in the proximal end of the graft. However, adjacent the heart the flow rate of blood through the aorta is so high that the risk of dislocation of the proximal stent is considerable.

In a particular lethal kind of aortic aneurysm the aortic wall is dissected to form a bogus lumen that establishes a parallel flow path for blood. The only method of repair is open surgery. In a so-called elephant trunk procedure, a stented distal end of a secondary graft pad is fixed in the descending aorta, and the proximal end of the secondary graft part is sutured to a primary graft part that is placed in the ascending aorta and anastomosed to the branch arteries carotis *communis*, subclavia and truncus brachiocephalicus.

During the operation the patient is subjected to cardiac arrest and systemic circulatory arrest, and although the patient has been cooled to a very low body temperature, such as 16° C. and selective cerebral perfusion is performed, the duration of the operation is a critical factor.

Dissections of the type in which the ascending aorta is involved pose a particular problem. With prior art techniques the mortality rate is 75% within 24 hours of initiation of the condition and 90% within one week. The surgeon thus has an extremely short time to prepare and perform surgery.

U.S. Pat. No. 6,773,457 discloses an aortic graft device which includes a graft portion and a corrugated or elephant trunk portion integral with and extending from the graft portion. The device is designed to be fitted to the aorta descendens. The corrugated portion, when fitted to a patient, forms the ascending portion of the device and is able to flex to the shape of the ascending aortic section in which it is placed. The device is fixed in place by locating it into the patient's previously opened aorta while the elephant trunk is everted into the graft portion. The surgeon sutures the rounded edge at the fold to the aortic wall, after which the trunk is fully unfolded. A problem with this procedure is that a surgeon has difficulties in suturing as a result of the fact that the rounded edge is thin, limp and lacks springiness. As a result of this, the suturing operation can take longer than necessary, which is undesirable and potentially dangerous.

French Patent Application number 2,777,450 discloses a stent graft which is provided with an elephant trunk and fixing mechanisms at both ends of the device. The upper end of the stent graft section is provided with an annular fixing band therearound which is fixed to a lumen-external band by rivets or sutures. The elephant trunk can be fixed to the lumen wall by suturing. The device disclosed in this document is not intended for location in the aorta descendens and is fitted in a different manner to the manner of fitting of the device of U.S. Pat. No. 6,773,457 discussed above.

SUMMARY OF THE INVENTION

The present invention seeks to provide an improved aortic graft device and an improved method of fitting an aortic graft device.

According to an aspect of the present invention, there is provided an aortic medical implant including a graft portion, a corrugated portion integral with and extending from the graft portion, and a fixing ring substantially at the junction between the graft and corrugated portions.

The fixing ring provides a volume of fixing material into which sutures can be passed. This considerably facilitates the process of suturing the device to the inside wall of the aorta, thereby making the sutures more secure and speeding up the surgical procedure. Thus, not only can the device be fitted better by the provision of the suture ring but the faster fitting operation can significantly reduce patient trauma and reduce the risk of patient mortality during the surgical procedure.

The fixing ring preferably provides for a blood tight connection to the lumen wall.

Advantageously, the fixing ring extends beyond the outer perimeter of the graft and/or corrugated sections. In an embodiment, the fixing ring extends beyond the radial perimeter of the graft and corrugated section combination when they are in their fully extended configurations.

In another embodiment, the fixing ring is located between the graft and corrugated portions in the longitudinal direction of the medical implant, such that when the corrugated portion is everted or folded into the graft portion the ring extends at a rounded suturing edge of the device.

Preferably, the fixing ring is made of a material which is stiffer than the material of either of the graft or corrugated portion. This has the advantage of providing a stable structure into which sutures can be passed. The material of the ring is preferably as stiff as possible without compromising the ease of passing a needle and suture thread therethrough.

Advantageously, the fixing ring is made of a foam or rubber like material. It could also be made of the same materials as other medical prostheses, such as heart valves.

According to another aspect of the present invention, there is provided a method of fixing an aortic medical implant provided with a graft portion and a corrugated portion integral with and extending from the graft portion, and a fixing ring substantially at the junction between the graft and corrugated portions; including the steps of providing the device with the corrugated portion everted into the graft portion, suturing the device to the internal aortic wall of a patient by passing sutures through the fixing ring and the lumen wall and everting the corrugated portion so as to extend beyond the graft portion in a deployed condition.

The fixing of the device in this described manner makes it possible for the device to be fixed to a portion of the aortic wall in the vicinity of the three branch arteries on the aortic arch. The anchoring can be made to the distal side of the arteria subclavia at least at the upper portion of the aortic arch and possibly in an annular pattern following the aortic wall.

For cases where the device is to be located over the branch arteries on the aortic arch, the graft portion can be provided with three corresponding side branches or with three windows to accommodate such side branches. In the preferred embodiment, the descending portion of the graft portion is non-corrugated at least at the fixing point and preferably along its full length. The non-corrugated area makes it easier to obtain a blood tight connection between the aortic graft device and any tubular member connected to it. The descending graft portion is preferably provided with at least one stent, and preferably provided with at least two stents, which are located near the fixing ring and at the distal opening, respectively. The stent resiliently acts on the graft portion to keep it open and non-kinking. The graft portion may have a length of at least 20 mm. The distal end area can be utilized to couple or anastomose the graft portion to either a secondary graft or to the aortic wall. It is possible to perform suturing in the distal end area but it is likewise possible to use the smooth surface character in the distal end area to obtain a pressure-tight seal between the graft portion and any secondary graft.

The descending graft portion of the portion is preferably supported by a stent at least along the majority of its length. By stenting, the descending portion is kept fully open, even when it is subjected to compression or kinking actions on the exterior of the distal portion which may be hanging in a free-floating manner in the aortic vessel downstream of the anchoring area. This is particularly useful when a distal graft is to be connected to the aortic graft device during separate surgery.

In order to facilitate handling and placement of the graft device at least the ascending portion of the graft portion may be precurved. The precurved shape reduces the bending forces required to keep the proximal portion in position during suturing of the device and thus minimizes the time spent on correcting the location of the aortic graft device during such suturing. In an embodiment, precurving of the graft portion can be achieved by cutting out a double wedge shaped portion of the tubular graft material and the facing edges of the material then sewn together. The removal of the double wedge-shaped area results in a distinct or sharp bend in the graft part at the place of the removed material and allows on the one hand manufacturing of the graft part as a straight tubular part with uniform properties and on the other hand the more sharp bend can be obtained in a comparatively easy manner. This facilitates exact repair of the ascending aorta and the aorta valve. Moreover, the embodiment would also prevent kinking of the graft device.

It is also envisaged that the corrugated or elephant trunk portion may be pre-curved, in a similar manner to the way the graft portion may be pre-curved, as described above. It is preferred that the ascending portion has a length in the range of from 11 to 17 cm, that the descending portion has a stented length in the range of from 5 to 10 cm, and that said distal end area has a length in the range of from 2 to 3 cm. These features make the graft portion quite flexible.

In some embodiments the corrugated portion may include a lateral opening so that the surgeon does not need to spend additional time providing communication between the aorta vascular space inside the device and the aortic branch arteries.

For a dissection which extends into the area of the heart valve and depending on the actual circumstances such, as whether a coronary artery is involved in the dissection, it can be insufficient to repair only the aorta. If additional surgery is required on the heart valve, the device might also include an end portion with a heart valve.

BRIEF DESCRIPTION OF THE DRAWINGS

Embodiments of the present invention are described below, by way of example only, with reference to the accompanying drawings, in which.

DETAILED DESCRIPTION

Figure 1:
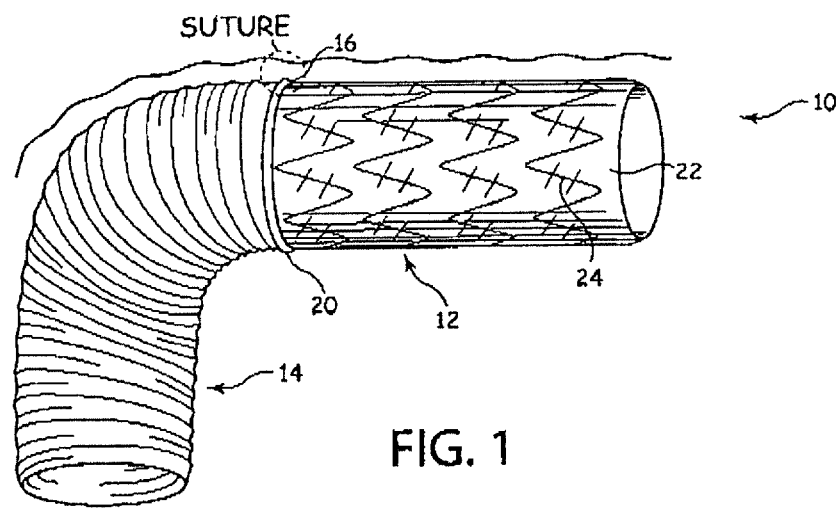
FIG. 1 shows a side elevational view of a preferred embodiment of aortic graft device.

Referring to FIG. 1, the aortic graft implant 10 shown includes an aortic graft section 12 and a corrugated or elephant trunk section 14. The aortic graft section 12 is tubular and has a proximal end 16 with a proximal opening 18 (not visible in FIG. 1). In the present context proximal is used to denote locations closer to the heart or in an upstream direction relative to aortic blood flow, whereas distal denotes locations more distant from the heart.

The graft section 12 and any possible graft extensions thereto which are provided can be made of a pliable material, such as expanded polytetrafluoroethylene (PTFE), woven polyester or another biocompatible material, for long term stability in the vascular system. Graft materials are well known in the art and the material can also include biodegradable strands as part of the material.

The graft section 12 is at least partially non-corrugated. It can have corrugations along part of its length and/or circumference but it is preferably non-corrugated along its complete length. It can be free of stents along its entire length but it is preferably at least partially stented, such as by a stent 24 located at the distal opening 22. In the preferred embodiment, there is provided a plurality of stents 24 along the length of the graft portion 12.

Stent 24 is of well known construction. It can be, for example, a so-called Gianturco Z-stent or any other stent of expandable or self-expandable type. It or they can typically be made of Nitinol, stainless steel or other biocompatible material. The or each stent 24 is typically placed inside the tubular graft material but can in the alternative be placed on the outside of the tubular material, which is then fastened to the stent struts. The stent or stents 24 can also be integrated in the graft material itself.

The length of the graft section 12 is of generally conventional size, for example from 7 cm to 13 cm.

The diameter of the graft section 12 may be in the range from 22 mm to 38 mm, preferably from 30 mm to 34 mm, such as about 32 mm. The tubular graft material has typically an even diameter along its length when it is manufactured and some variations in diameter can result from the crimping of the corrugated portion 14. However, it is also possible to make the device of two separate tubular parts of different diameter, if the corrugated portion 14 is to be of a diameter different from the graft portion 12 of the device 10. The elephant trunk section 14 is corrugated or crimped in order to promote setting of the section 14 in a curved shape. The elephant trunk section 14 extends from the graft section 12 and in the preferred embodiment is fixed thereto. This section 14 may be made of the same material as the graft section 12.

As is described below with reference to FIGS. 2 and 3 in particular, this section 14 is an ascending section, that is it extends proximally in the aorta relative to the graft section 12.

The trunk section 14 may have a length of 11 to 17 cm, although this could be varied as required for any particular patient or to suit the characteristics of the aneurism.

An anchoring member 20 is positioned at the junction of the two portions 12, 14. The anchoring member, in the preferred embodiment, is a ring or cuff 14 of material which is able to receive and hold sutures. It is preferably made from a relatively stiff material compared to the graft and corrugated section materials and is of a nature that it provides a volume of material which can be held by a surgeon during suturing.

The anchoring member can be made of foam, rubber, silicone or of graft material.

The anchoring member 20 may be fixed to an outside surface of the graft and/or trunk portions 12, 14, for example by suturing, by a suitable adhesive, by welding, by thermoforming or by any other suitable method. In some embodiments, the member 20 could be formed integrally with the graft and/or trunk portions 12, 14.

In another embodiment, the anchoring member 20 is located between the graft portion 12 and the trunk portion 14, so as in effect to form a bridge between the two.

It is also envisaged that the ring 16 might be formed from a rolled layer of graft material to provide a sufficient volume to hold sutures without needing for the sutures to pass through any of the lumen walls of the device.

There may be provided a plurality of anchoring members 20, for example longitudinally aligned and in close proximity to one another. In some embodiments, the anchoring member 20 may not be annular as shown. It could, for example, be of spiral form.

The anchoring member 20 thus provides a volume of material which can be easily handled by a surgeon, which can hold sutures and which can reliably form a blood tight seal with the lumen wall, without any puncturing of the lumen of the device 10 by the sutures.

Figure 2:
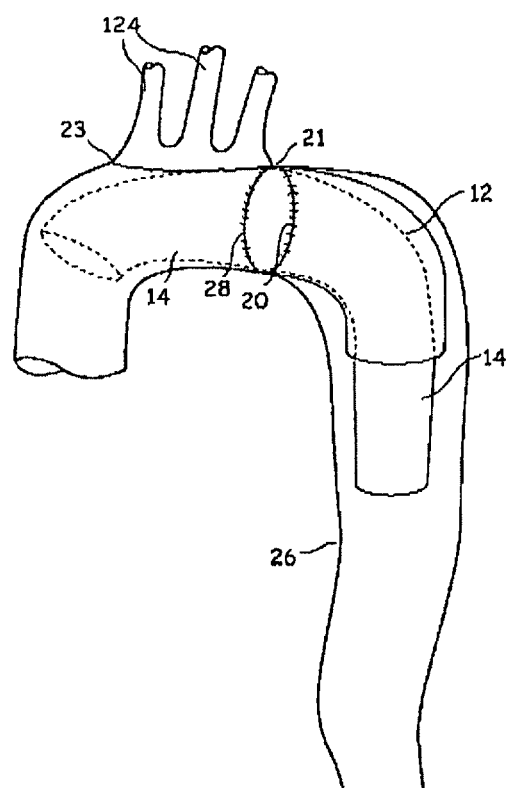
FIG. 2 shows in schematic form the embodiment of device of FIG. 1 during its fitting to an aorta of a patient.
Figure 3:
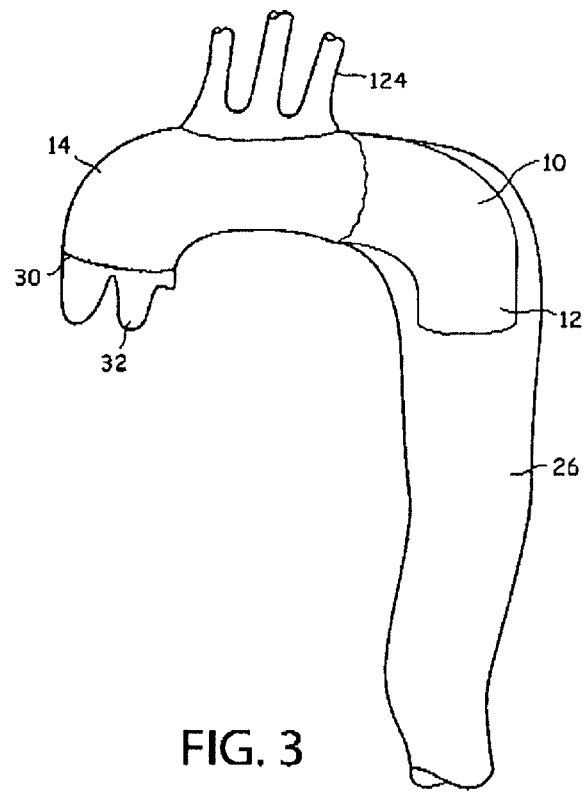
FIG. 3 shows the device in a deployed state.
Figure 4:
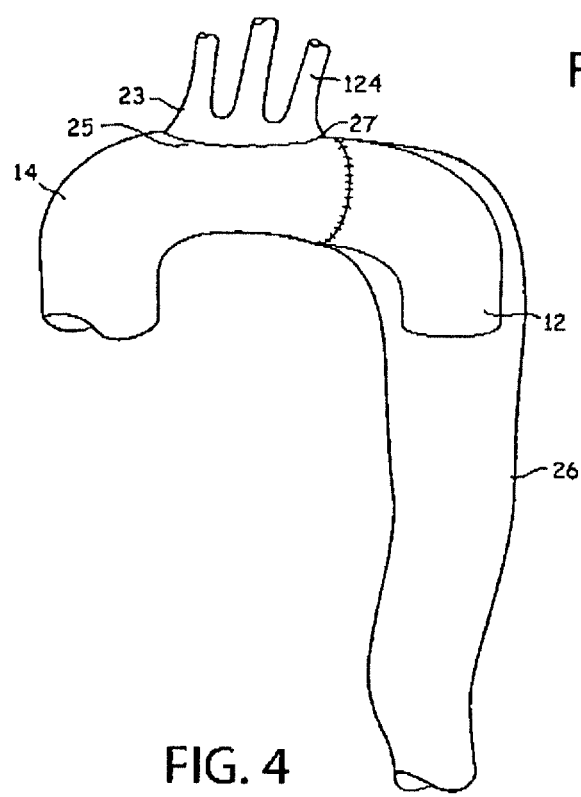
FIG. 4 shows an embodiment of deployed medical implant provided with an opening to accommodate the three major aortic branch arteries.

Other features of the anchoring member 20 will become apparent from the following description as to the deployment of the device 10 in a patient, for which reference is made to FIGS. 2 to 4 in particular.

After cooling the patient down and exposing the aortic arc through a sternotomy and performing cardiopulmonary bypass or systemic circulatory arrest, the proximal portion of the patient's aorta 26 is resected, thereby exposing a proximal end opening on the descending aorta 26 and a proximal end area at the three major branch arteries 24, in conventional manner.

The medical implant is provided in a mounting state in which the trunk portion 14 is everted so as to extend into and beyond the graft portion, such that the anchoring member 20 is at an end of the device 10, as shown in FIG. 2. The device 10 is placed into the descending aorta with the anchoring member 20 at the opening of the aorta. The anchoring member 20 can then be sutured to the internal aortic wall 21. As the anchoring member 20 has a useful volume, the surgeon can easily grasp the member 20 and can readily pass sutures 28 through the ring or annulus of the member 20. This considerably facilitates the surgeon's job of suturing the device 10 to the aorta. Furthermore, the provision of the anchoring member 20 ensures better blood-tight connection of the device 10 to the aorta, thereby ensuring more stable fitting of the device 10.

After fixing the device 10 to the aortic wall, the trunk portion 14 is everted to its normal deployed position, illustrated in FIG. 4.

In the example of this Figure, the trunk portion 14 is provided with an opening 24, the edges 25 of which can be sutured or stapled to the ends 23 of the aortic branches 24, in conventional manner.

At this point the surgeon can decide to insert a secondary graft (see, for example FIGS. 5 and 6) through the proximal opening 22 of the graft portion 12 and mount it in the ascending aorta 26 and/or to the trunk portion 14 of the device 10. In many cases the decision will be to postpone the placement of any secondary graft part for subsequent surgery in order to re-establish circulation as quickly as possible.

The rim area at the trunk opening 30 can be joined with the rim area of the aorta 26, such as by suturing or stapling, in this example adjacent the aortic valve 32.

The device 10 is then in the state illustrated in FIG. 3 and in a condition in which the patient's circulation can be re-established. The distal end of the graft portion 12 is hanging loose into the aorta 26. Depending upon the condition and desires of the patient it is then possible to proceed in numerous ways. One possibility is to open the patient from the side and secure the distal end 22 of the graft portion 12 to the aortic wall, such as by suturing, stapling or stenting. Another possibility is to add the distal graft extension 13 (shown in FIGS. 5 and 6), which can be achieved either by percutaneously introducing (for example, femorally) and intraluminally advancing graft extension 13 with a minimally invasive procedure or by performing open surgery where the patient is opened from the side and the secondary graft extension 13 is introduced after establishing suitable annulation and bypass.

Figure 5:
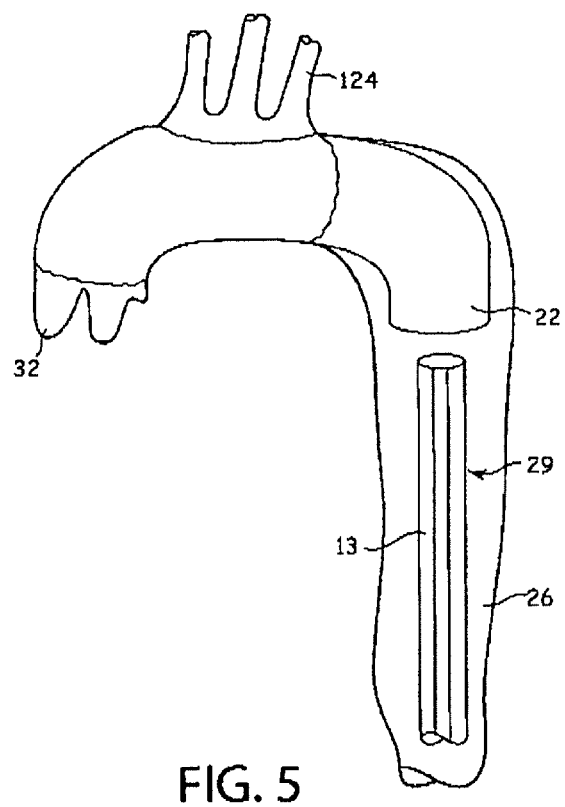
FIGS. 5 and 6 illustrate another example in which a secondary graft extension is fitted to the device of FIG. 3.
Figure 6:
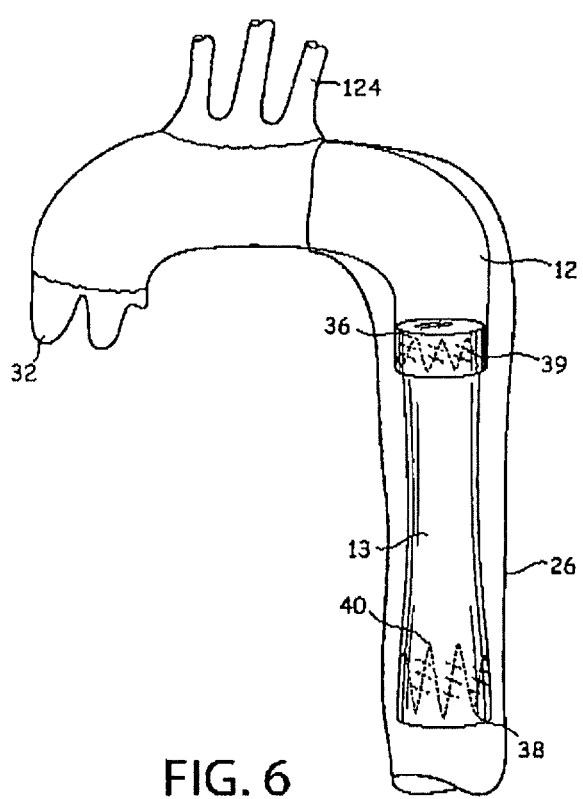

FIGS. 5 and 6 illustrate the introduction of a distal graft extension 13 held in a radially compressed state in an introducer 29. When the proximal end 36 of graft extension 13 is correctly located in the graft portion 12 this proximal end 36 is released from or expanded by the introducer 29 onto the internal wall of the graft section 12, into secure mutual engagement. Known connecting means are used to ensure such connection.

Subsequent to this, a distal end 38 of the graft extension 13 is located at the desired site of the aorta 26 and is fixed thereto, either by suturing, stapling or by stenting. FIG. 6 illustrates stenting with a distal-most stent 40 in the distal end.

In order to provide for curvature of the graft section 12 and/or of the trunk section 14, a double wedge-shaped area of the material can be cut away and the facing edges formed thereby joined together, such as by suturing. Such cutting and joining can be made to modify the contour of the aortic graft device to the shape of the aortic arch, thus preventing kinking of the graft and promoting accurate placement of the graft to the ascending aorta and its the sinotubular junction.

It is envisaged in some applications that a stent may be located within the graft/trunk sections in the region of the collar 16 to push the collar outwardly towards the lumen.

The invention claimed is:

1. A prosthesis comprising:
   a unitary tube of graft material, the unitary tube of graft material comprising:
   a stented graft portion having an outer perimeter, an inner lumen, a first end, a second end,
   a completely unstented crimped portion integrally formed with and extending from the first end of the stented graft portion to form a junction between the unstented crimped portion and the first end of stented graft portion, the unstented crimped portion having an outer perimeter, and the junction having a circumference,
   a plurality of independent ring stents extending from the junction to the second end of the stented graft portion including a first stent ring and a series of undulating ring stents extending distally from the first ring stent to the distal end of the stented graft portion,
   a collar substantially at the junction between the first end of the stented graft portion and the unstented crimped portion and extending about the circumference of the junction,
   at least one fenestration in the tube of graft material, and
   a branch extending from the at least one fenestration in the tube of graft material,
   wherein the first ring stent of the plurality of ring stents is disposed directly adjacent to the collar,
   wherein the collar extends radially away from and beyond the entire outer perimeters of both the stented graft portion and the unstented crimped portion, such that the collar is configured to provide an extended stable surface structure away from the outer perimeters of the stented graft portion and the unstented crimped portion for the passage of sutures without the passage of sutures into the lumens of either the stented graft portion or the unstented crimped portion.

2. The prosthesis of claim 1, wherein the ring stents consist of nitinol.

3. The prosthesis of claim 2, wherein a plurality of the plurality of the ring stents are undulating stents.

4. The prosthesis of claim 1, wherein the ring stents are integrated nitinol stents.

5. The prosthesis of claim 3, wherein the ring stents are integrated.

6. The prosthesis of claim 1, wherein the collar is formed from a material that is different than the graft material of the one of or both the unstented crimped portion and the stented graft portion.

7. The prosthesis of claim 1, wherein the unstented crimped portion and the stented graft portion are of substantially equal diameter.

8. The prosthesis of claim 1, wherein the collar consists of the same graft material as the unitary tube of graft material.

9. The prosthesis of claim 8, wherein the collar is formed integrally with the unitary tube of graft material.

10. The prosthesis of claim 1, wherein the stented graft portion and the unstented crimped portion are formed from a single tube of graft material.

11. The prosthesis of claim 1, wherein the at least one fenestration comprises three fenestrations in the unstented crimped portion and each fenestration has a branch secured to the unstented crimped portion and extending away from the unstented crimped portion.

12. A prosthesis comprising:
    a unitary tube of graft material, the unitary tube of graft material comprising:
    a stented graft portion having an outer perimeter, an outer surface, an inner lumen, a first end, a second end,
    a completely unstented crimped portion integrally formed with and extending from the first end of the stented graft portion to form a junction between the unstented crimped portion and the first end of stented graft portion, the unstented crimped portion having an outer perimeter, and the junction having a circumference,
    a plurality of independent ring stents extending from the junction to the second end of the stented graft portion including a first stent ring and a series of undulating ring stent extending from the first ring stent to the second end of the stented graft portion,
    a collar substantially at the junction between the first end of the stented graft portion and the unstented crimped portion and extending about the circumference of the junction,
    a plurality of fenestrations in a sidewall the graft material, and
    a branch attached to the graft material at each of the fenestrations,
    wherein the first ring stent is disposed directly adjacent to the collar,
    wherein the collar extends radially away from and beyond the entire outer perimeters of both the stented graft portion and the unstented crimped portion, such that the collar is configured to provide an extended stable surface structure away from the outer perimeters of the stented graft portion and the unstented crimped portion for the passage of sutures without the passage of sutures into the lumens of either the stented graft portion or the unstented crimped portion,
    wherein one or both of the unstented crimped portion and stented graft portion is pre-curved, and
    wherein the plurality of independent ring stents are comprised of nitinol.

13. The prosthesis of claim 12, wherein the unstented crimped portion and the stented graft portion are of equal diameter.

14. The prosthesis of claim 12, wherein the junction between the unstented crimped portion and the stented graft portion is seamless.

15. A prosthesis comprising:
    a unitary tube of graft material, the tube of graft material comprising:
    a stented graft portion having an outer perimeter, an inner lumen, a first end, a second end,
    an unstented crimped portion integrally formed with and extending from the first end of the stented graft portion to form a junction between the unstented crimped portion and the first end of stented graft portion, the unstented crimped portion having an outer perimeter, and the junction having a circumference, a collar at the junction between the first end of the stented graft portion and the unstented crimped portion and extending about the circumference of the junction, a first ring stent disposed directly adjacent the collar on the stented graft portion, a plurality of independent undulating ring stents extending from the first ring stent to the second end of the stented graft portion, at least one fenestration in the graft material, and a branch attached to the graft material at the fenestration and in fluid communication with fenestration;

wherein the collar extends radially away from and beyond the entire outer perimeters of both the stented graft portion and the unstented crimped portion, such that the collar is configured to provide an extended stable surface structure away from the outer perimeters of the stented graft portion and the unstented crimped portion for the passage of sutures without the passage of sutures into the lumens of either the stented graft portion or the unstented crimped portion.

16. The prosthesis of claim 15, wherein the stented graft portion and the unstented crimped portion are formed from a single tube of graft material.

17. The prosthesis of claim 15, wherein one of or both the unstented crimp portion and the stented portion is pre-curved.

18. The prosthesis of claim 15, wherein the unstented crimped portion and the stented graft portion are the same diameter.

19. The prosthesis of claim 15, wherein the unstented crimped portion and the stented graft portion are different diameters.

20. A prosthesis comprising:

a unitary tube of graft material, the unitary tube of graft material comprising:

a stented graft portion having an outer perimeter, an inner lumen, a first end, a second end, a completely unstented crimped portion integrally formed with and extending from the first end of the stented graft portion to form a junction between the unstented crimped portion and the first end of stented graft portion, the unstented crimped portion having an outer perimeter, and the junction having a circumference, a plurality of independent ring stents extending from the junction to the second end of the stented graft portion including a first stent ring and a series of undulating ring stents extending distally from the first ring stent to the distal end of the stented graft portion, a collar substantially at the junction between the first end of the stented graft portion and the unstented crimped portion and extending about the circumference of the junction, at least one lateral opening in the unstented crimped region configured to accommodate aortic branch arteries, wherein the first ring stent of the plurality of ring stents is disposed directly adjacent to the collar, wherein the collar extends radially away from and beyond the entire outer perimeters of both the stented graft portion and the unstented crimped portion, such that the collar is configured to provide an extended stable surface structure away from the outer perimeters of the stented graft portion and the unstented crimped portion for the passage of sutures without the passage of sutures into the lumens of either the stented graft portion or the unstented crimped portion.

* * * * *